US008518329B2

(12) United States Patent
Hassibi et al.

(10) Patent No.: US 8,518,329 B2
(45) Date of Patent: Aug. 27, 2013

(54) INCORPORATING CMOS INTEGRATED CIRCUITS IN THE DESIGN OF AFFINITY-BASED BIOSENSOR SYSTEMS

(75) Inventors: Arjang Hassibi, Austin, TX (US); Byungchul Jang, Ridgeland, MS (US); Arun Manickam, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/417,661

(22) Filed: Mar. 12, 2012

(65) Prior Publication Data
US 2012/0168306 A1 Jul. 5, 2012

Related U.S. Application Data

(62) Division of application No. 12/617,794, filed on Nov. 13, 2009, now abandoned.

(60) Provisional application No. 61/115,485, filed on Nov. 17, 2008.

(51) Int. Cl.
| | |
|---|---|
| *G01N 27/00* | (2006.01) |
| *G01N 21/75* | (2006.01) |
| *G01N 27/403* | (2006.01) |
| *C12M 1/00* | (2006.01) |
| *C40B 30/04* | (2006.01) |

(52) U.S. Cl.
USPC ... 422/82.03; 422/400; 422/402; 204/403.01; 506/9; 257/253

(58) Field of Classification Search
USPC .............. 422/400, 402; 204/403.01; 506/9; 257/253
See application file for complete search history.

(56) References Cited

U.S. PATENT DOCUMENTS

| | | | |
|---|---|---|---|
| 2005/0006234 A1 | 1/2005 | Hassibi | |
| 2006/0208254 A1* | 9/2006 | Goodman et al. | 257/40 |
| 2008/0081769 A1 | 4/2008 | Hassibi | |
| 2009/0111207 A1* | 4/2009 | Choumane et al. | 438/70 |
| 2012/0088682 A1* | 4/2012 | Rothberg et al. | 506/9 |

OTHER PUBLICATIONS

Schienle, M., et al., "A Fully Electronic DNA Sensor with 128 Positions and In-Pixel ADC," IEEE JSSC, vol. 39, pp. 2438-2445, Dec. 2004.

Hassibi, A., et al., "A Programmable 0.18 micrometer CMOS Electrochemical Sensor Microarray for Biomedical Detection," IEEE Sensors Journal, vol. 60, pp. 1380-1388, Dec. 2006.

Augustyniak, M., et al., "A 24×16 CMOS-Based Chronocoulometric DNA Microarray," ISSCC Tech. Dig., pp. 59-68, 2006.

Han, Shu-Jen, et al., "A High-Density Magnetoresistive Biosensor Array with Drift-Compensation Mechanism," ISSCC Tech. Dig., pp. 168-169, 2007.

(Continued)

*Primary Examiner* — Dean Kwak
(74) *Attorney, Agent, or Firm* — Winstead P.C.

(57) ABSTRACT

A biosensor system incorporating CMOS integrated circuits. In one type of biosensor system, the biosensor system includes a silicon substrate. The biosensor system further includes active devices fabricated on the silicon substrate. Additionally, the biosensor system includes a plurality of metal layers stacked on top of the active devices. Furthermore, the biosensor system includes a passivation layer covering a top metal layer, where the passivation layer includes an opening configured to expose the top metal layer, where the opening is used as a sensing electrode. Additionally, the biosensor system includes a plurality of probes attached to the sensing electrode.

5 Claims, 12 Drawing Sheets

(56) References Cited

OTHER PUBLICATIONS

Parikh, Samir, et al., "A CMOS Image Sensor for DNA Microarray," IEEE CICC, pp. 821-824, Sep. 2007.
Eltoukhy, Helmy, et al., "A 0.18-µm CMOS Bioluminescence Lab-On-Chip," IEEE J. Solid State Circuits, vol. 41, pp. 651-662, Mar. 2006.
Wong et al., "A CMOS-Integrated 'ISFET-Operational Amplifier' chemical Sensor Employing Differential Sensing," IEEE Transactions on Electron Devics, vol. 36, No. 3, Mar. 1989.
Hammond et al., "Design of a Single-Chip pH Sensor Using a Conventional 0.6-µm CMOS Process," IEEE Sensors Journal, vol. 4, No. 6, Dec. 2004.
Caillat et al., "Biochips on CMOS: an active matrix address array for DNA analysis," Sensors and Actuators B 61 (1999) 154-162.

* cited by examiner

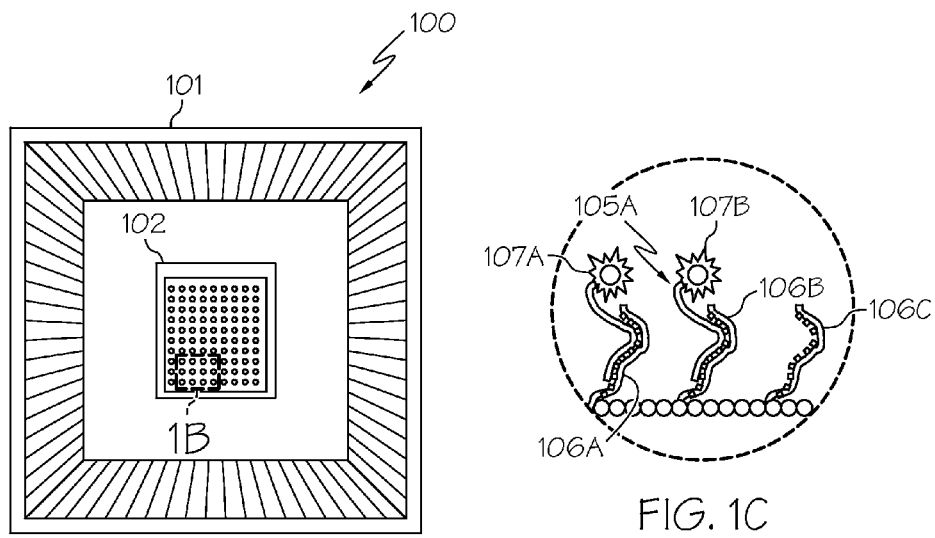
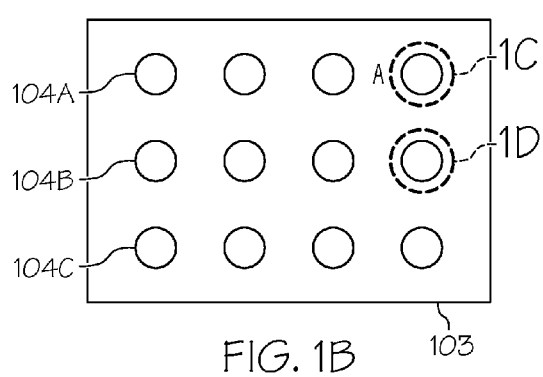
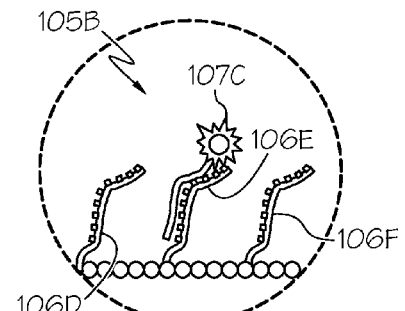
FIG. 1A
FIG. 1B
FIG. 1C
FIG. 1D

INCORPORATING CMOS INTEGRATED CIRCUITS IN THE DESIGN OF AFFINITY-BASED BIOSENSOR SYSTEMS

CROSS-REFERENCE TO RELATED APPLICATIONS

The present application is a divisional application of co-pending U.S. patent application Ser. No. 12/617,794, entitled "Incorporating CMOS Integrated Circuits in the Design of Affinity-Based Biosensor Systems," filed Nov. 13, 2009, which is incorporated by reference herein. The present application claims priority benefits to U.S. patent application Ser. No. 12/617,794 under 35 U.S.C. §121. U.S. patent application Ser. No. 12/617,794 claims priority under 35 U.S.C. §119(e) to U.S. Provisional Patent Application Ser. No. 61/115,485, filed Nov. 17, 2008 which is incorporated herein by reference.

TECHNICAL FIELD

The present invention relates generally to biosensor systems, and more particularly to incorporating CMOS integrated circuits in the design of affinity-based biosensor systems.

BACKGROUND OF THE INVENTION

Affinity-based detection is a fundamental method to identify and measure the abundance of biological and biochemical analytes and is one of the most important analytical methods in biotechnology. Affinity-based detectors (or so-called biosensors in case of detecting biological analytes) take advantage of the selective interaction and binding (affinity) of the target analyte with immobilized capturing probes to specifically capture the target analyte onto a solid surface. A goal of a detection platform is to facilitate specific capturing and ultimately to produce a detectable signal based on the captured analytes. The generated signals correlate with the presence of the target analytes in the sample (e.g., toxins, polymers, hormones, DNA strands, proteins, bacteria, etc.), and hence are used to estimate their abundance.

To create target-specific signals in biosensors, the target analytes in the sample volume first need to collide with the capturing layer, interact and bind to the probes, and ultimately take part in a transduction process (i.e., a physiochemical process which produces certain measurable electrical, mechanical, or optical parameters produced solely by the captured entities). The analyte motion in typical biosensor settings (e.g., aqueous biological mediums) is dominated by diffusion spreading, which from a microscopic point of view is a probabilistic mass-transfer process (i.e., random walk events for a single analyte molecule). Accordingly, the analyte collisions with the probes become probabilistic processes. Moreover, because of the quantum-mechanical nature of chemical bond formation, interactions between probes and analytes, are also probabilistic, adding more uncertainty to the capturing procedure. On top of these two processes which can be considered the biochemical noise of the system, there may also be a detector and a readout circuitry (e.g., optical scanners for fluorescent-based transducers), which likely add additional noise to the already noisy signal.

Besides the inevitable uncertainty associated with the target analyte capturing and detecting, in all practical biosensors, binding of other species to the probes (non-specific binding) is also possible. Non-specific binding (e.g., cross-hybridization in DNA microarrays) is generally less probable than the specific binding when target analytes and the interfering species have the same abundance. Nonetheless, when the concentration of the non-specific species becomes much higher than the target analyte, non-specific bindings (or essentially interference) may dominate the measured signal and hence limit the minimum-detectable-level (MDL). In biosensors, the MDL may be either biochemical noise or interference-limited, while the highest detection level (HDL), is solely a function of capturing probe density and its saturation level.

Due to such impediments, as of today, the accuracy of biosensors systems does not satisfy the stringent requirements of many high-performance biotechnology applications in molecular diagnostics and forensics. In addition, biosensors systems have not successfully made the transition to portable and compact point-of-care devices because their detection platforms still consist of fluidic systems and bulky detectors.

One proposed solution to address the challenges of biosensor systems is to use semiconductor fabrication technologies to build compact, high-performance, and cost-efficient biosensor systems. It is envisioned that such systems (i.e., lab-on-a-chip platforms), include not only the fluidic (macro or micro) systems and sample preparation processes, but also the integrated transducers.

The challenge of designing sample preparation modules in biosensors, to some extent, has been addressed in recent years, particularly in the form of micro-fluidic and automated liquid handling systems; however, the integration of the detector and readout circuitry has not been addressed. One reason why the integration of the detector and readout circuitry has not been addressed is the technical challenge of manufacturing transducers using custom surface and bulk MEMS procedures. Another reason is performance and cost justification of monolithic integration of all components.

In recent years, the idea of employing Complementary Metal-oxide-semiconductor (CMOS) fabrication processes, which are the most robust and widely used fabrication processes in the semiconductor industry, for biosensors has emerged. The rationale behind this, as opposed to using MEMS or other custom processes, is the unmatched yield, cost-efficiency, and the integration capabilities of CMOS processes. While CMOS processes, from the electronic design point of view, offer huge degree of design flexibility and system integration, they are not very flexible in terms of form factor, transducer design and interface integration. Challenges remain in designing biosensors to take advantage of the CMOS fabrication method. The primary design challenge using CMOS technology is the interface design between the assay and integrated chip (IC) which requires additional post-fabrication processes for compatibility in detecting targets (e.g., analytes).

Therefore, there is a need in the art for incorporating the use of CMOS fabrication processes in the design of affinity-based biosensor systems.

BRIEF SUMMARY

In one embodiment of the present invention, a biosensor system comprises a silicon substrate. The biosensor system further comprises active devices fabricated on the silicon substrate. Additionally, the biosensor system comprises a plurality of metal layers stacked on top of the active devices. Furthermore, the biosensor system comprises a passivation layer covering a top metal layer of the plurality of metal layers in order to protect the plurality of metal layers, where the passivation layer comprises an opening configured to expose the top metal layer, where the opening is used as a sensing electrode. Additionally, the biosensor system comprises a plurality of probes attached to the sensing electrode.

The foregoing has outlined rather generally the features and technical advantages of one or more embodiments of the present invention in order that the detailed description of the present invention that follows may be better understood. Additional features and advantages of the present invention will be described hereinafter which may form the subject of the claims of the present invention.

BRIEF DESCRIPTION OF THE SEVERAL VIEWS OF THE DRAWINGS

A better understanding of the present invention can be obtained when the following detailed description is considered in conjunction with the following drawings, in which:

FIGS. 1A-D illustrate a fully integrated fluorescent-based biosensor microarray system in accordance with an embodiment of the present invention;

DETAILED DESCRIPTION

In the following description, numerous specific details are set forth to provide a thorough understanding of the present invention. However, it will be apparent to those skilled in the art that the present invention may be practiced without such specific details. In other instances, well-known circuits have been shown in block diagram form in order not to obscure the present invention in unnecessary detail. For the most part, details considering timing considerations and the like have been omitted inasmuch as such details are not necessary to obtain a complete understanding of the present invention and are within the skills of persons of ordinary skill in the relevant art.

As discussed in the Background section, biosensors are one of the most important analytical tools in biotechnology today. These detection systems take advantage of the selective interaction and binding of certain biological molecules to identify and detect different analytes such as toxins, hormones, DNA strands, proteins, bacteria, etc. The fundamental advantage of array based biosensors, which compensate for their limited signal-to-noise ratio ("SNR"), is their capability to detect multiple analytes simultaneously. Today, densely packed biosensor arrays (i.e., microarrays) which detect hundreds or even thousands of different analytes are an integral part of biotechnology.

Certain emerging biotechnology applications, such as high-throughput molecular screening and point-of-use (PoU) molecular diagnostics, necessitate biosensor integration, particularly the interfacing of the biochemical part (assay) with the transducer and the readout circuitry. This is mainly due to the stringent requirements of applications which demand compact, cost-efficient, and disposable systems with a high production yield and robust functionality; a goal which silicon-based integrated circuits technology in general, and CMOS processes in particular can provide.

The dominant biosensor and microarray detection modality is visible-range fluorescence spectroscopy using fluorescent labels as the reporters for target analyte molecules. While alternative "label-free" transduction methods (e.g., electrochemical or magnetic) exist today, fluorescent-based detection still remains the most sensitive and robust method, particularly in DNA detection application. The performance advantages of this detection method over other methods originate from the uniqueness of fluorescence phenomenon which makes the generated signals very specific and less susceptible to biological interference.

Figure 3:
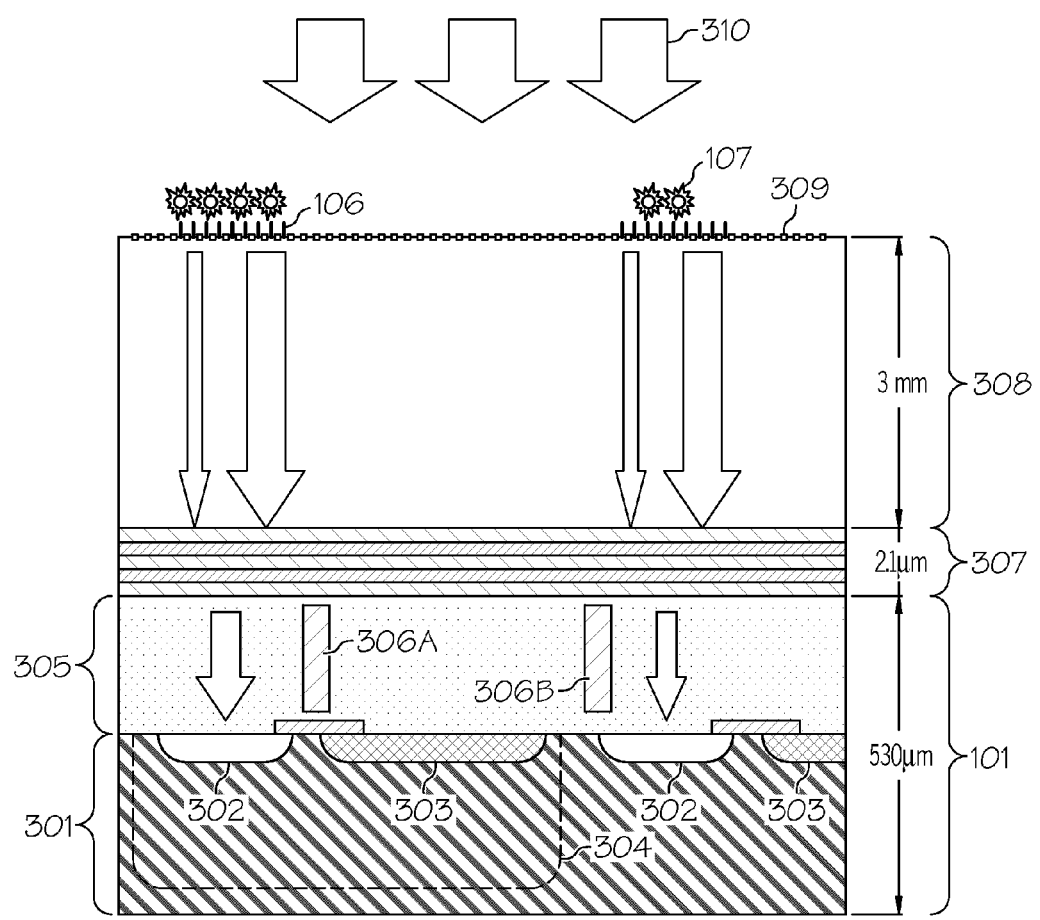
FIG. 3 illustrates optically coupling the capturing probes with the CMOS detector using a fiber-optical faceplate in accordance with an embodiment of the present invention.

Referring to FIGS. 1A-D, FIG. 1-D illustrate a fully integrated fluorescent-based biosensor microarray system 100 in accordance with an embodiment of the present invention. System 100, as shown in FIG. 1A, includes a packaged CMOS integrated circuit 101 with a sensing area 102. In one embodiment, sensing area 102 has a thickness of approximately 3 millimeters. Details of sensing area 102 are provided further below in connection with FIG. 3 showing the transducers, emission filter, and readout circuitry, including the analog-to-digital converter (ADC).

To visualize the structures of sensing area 102 for biological significance, a fluorescent image 103 of a portion of sensing area 102 is taken as shown in FIG. 1B. Fluorescent imaging techniques, include, but are not limited to electron microscopy, x-ray crystallography, nuclear magnetic resonance spectroscopy and atomic force microscopy. Fluorescent image 103 illustrates photo-detectors 104A-C. Photo-detectors 104A-C may collectively or individually be referred to as photo-detectors 104 or photo-detector 104, respectively. System 100 may include any number of photo-detectors 104 and the number of photo-detectors 104 shown in FIG. 1B is illustrative.

Fluorescent image 103 further illustrates targets (e.g., analytes) 105A-B. Targets 105A-B may collectively or individually be referred to as targets 105 or target 105, respectively. System 100 may include any number of targets 105 and the number of targets 105 shown in FIGS. 1C and 1D is illustrative.

For each target 105, a fluorescent label is captured by a DNA capturing probe. For example, capturing probes 106A-C are used to capture fluorophores 107A-B using a process referred to as fluorescent labeling in connection with target 105A. Similarly, capturing probes 106D-F are used to capture fluorophore 107C in connection with target 105B.

Capturing probes 106A-F may collectively or individually be referred to as capturing probes 106 or capturing probe 106, respectively. Further, fluorophores 107A-C may collectively or individually be referred to as fluorophores 107 or fluorophore 107, respectively. System 100 may include any number of capturing probes 106 and fluorophores 107 and the number of capturing probes 106 and fluorophores 107 shown in FIGS. 1C and 1D is illustrative.

While system 100 is designed and fabricated for DNA microarrays, the achieved specifications are well suited for other biosensor applications.

The foremost challenge in designing fluorescent-based detectors is the proper excitation of labels and the detection of their emitted signal. The photon absorption of the fluorescent label, denoted by A in FIGS. 1A-D, exposed to an incident photon flux, $F_X$, obeys the Beer-Lambert law. For a thin layer of fluorescent labels, the absorption is given by $$A = F_X[1 - e^{-a_0(\lambda)N}] \approx F_X a_0(\lambda)N, \quad (1)$$

where N is the surface concentration of labels with extinction coefficient of $a_0(\lambda)$. The total isotropic photon emission, $I_E$, as a function of $Q_Y$, the fluorescence quantum, is given then by $$I_E = Q_Y A \approx Q_Y F_X a_0(\lambda) N \quad (2)$$

The major function of a fluorescent-based biosensor is to measure N using $I_E$ based on equation (2) in the presence of $F_X$. Although $F_X$ generally has a slightly different wavelength from $I_E$, it is typically 4-5 orders larger and therefore needs to be blocked during detection.

Figure 2:
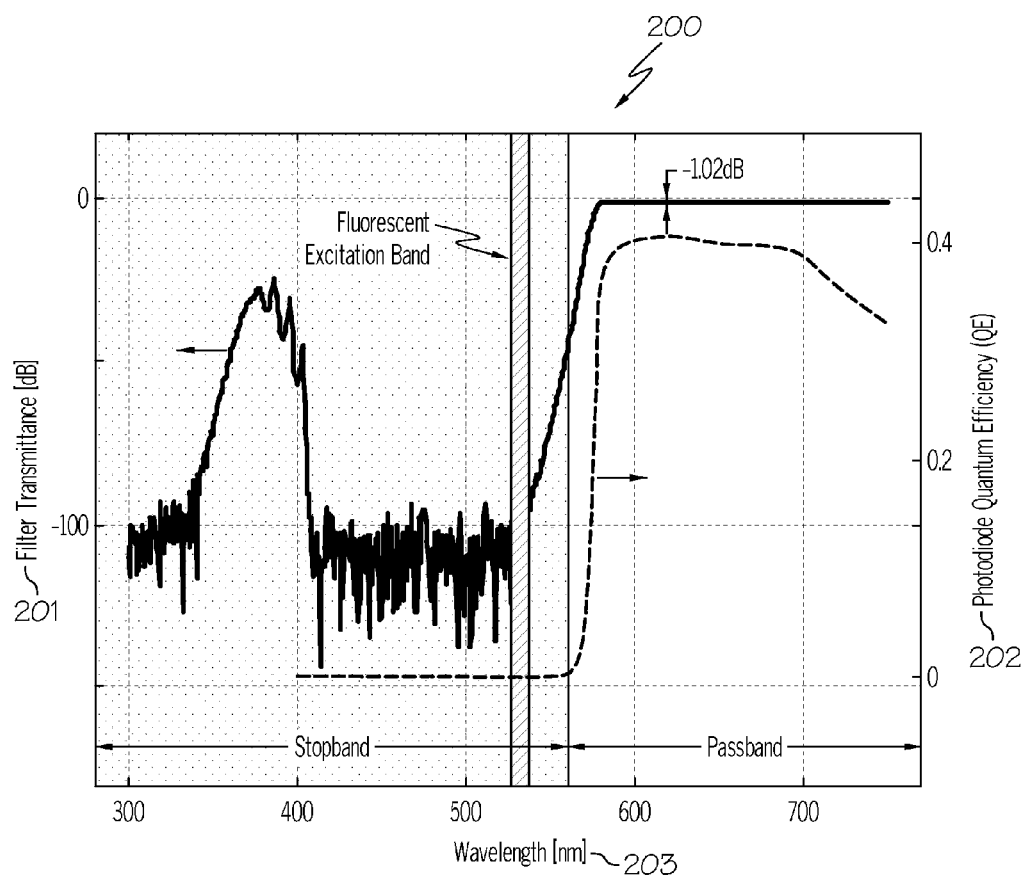
FIG. 2 is a graph of the filter transmittance and photodiode quantum efficiency versus the wavelength in accordance with an embodiment of the present invention.

In one embodiment, a low-power diode pumped solid-state (DPSS) green laser is used with an output wavelength of 532 nm to create $F_X$. To block $F_X$ from reaching integrated photodetector 104, a multi-layer thin film dielectric long-pass (edge) optical filter (discussed below in connection with FIG. 3) is designed and fabricated. In one embodiment, the optical filter comprises 20 layers of ZnS (n=2.30) and $Na_3AlF_6$ (n=1.35) with an overall thickness of 2.1 μm. The measured transmittance of the filter is illustrated in FIG. 2. The filter rejects $F_X$ by 98 dB at 532 nm, while having approximately 1 dB loss in the optical passband.

In connection with the filter discussed above, FIG. 2 is a graph 200 of the filter transmittance (in dB) 201 and photodiode quantum efficiency (QE) 202 versus the wavelength (in nanometers) 203 in accordance with an embodiment of the present invention. Referring to FIG. 2, FIG. 2 illustrates the filter response which rejected (about −100 dB) the light that was below 532 nm (at the fluorescent excitation band) while passing light that was greater than 560 nm. The range of frequencies that are attenuated are referred to as "stopband" as shown in FIG. 2; whereas, the range of frequencies that can pass through the filter without being attenuated are referred to as "passband" as shown in FIG. 2. Further, FIG. 2 illustrates that the emitted light of 570 nm wavelength will not be attenuated very much thereby allowing the transducer and detection circuitry (discussed below in connection with FIG. 10) using the CMOS process to detect this light signal. FIG. 2 further illustrates the efficiency of the CMOS transducer. The plot on the right of FIG. 2 represents how a transducer (e.g., photodiode 302 of FIG. 3) efficiently converts light energy (e.g., photon energy) into electrical energy.

In order to integrate the biochemical part of the assay with fluorescent detector 104 (FIG. 1B), capturing probes 106 (FIGS. 1C and 1D) are optically coupled to the CMOS detector using a fiber-optical faceplate (FOF) placed on top of CMOS integrated circuit 101 (FIG. 1A) as shown in FIG. 3 in accordance with an embodiment of the present invention. Referring to FIG. 3, in conjunction with FIGS. 1A-D, in one embodiment, CMOS sensor array chip 101 has a thickness of approximately 530 micrometers which includes a silicon substrate 301 containing a photodiode 302 and readout circuitry 303 forming a pixel 304. On top of silicon substrate 301 may include a dielectric layer 305, such as silicon dioxide, containing metal "curtains" 306A-B. Curtains 306A-B may collectively or individually be referred to as curtains 306 or curtain 306, respectively. Curtains 306 may be employed for further optical shielding against optical crosstalk by taking advantages of integrated circuit structures in addition to physical distance between neighboring pixels. In one embodiment, curtains 306 are composed of vias and metal layers (shown in FIG. 8A) and may encompass the entire photodiode 302. Chip 101 may include any number of curtains 306 and the number of curtains 306 shown in FIG. 3 is illustrative.

FIG. 3 further illustrates an optical filter 307 (long-pass filter discussed above) residing on the top of chip 101. In one embodiment, optical filter 307 has a thickness of approximately 2.1 micrometers. On top of long pass filter 307 may reside a fiber-optical faceplate 308. In one embodiment, optical filter 307 includes layers of materials with a dissimilar refractive index.

In one embodiment, optical filter 307 is fabricated on the bottom of fiber-optical faceplate 308 and on the top of chip 101. Optical filter 307 prohibits light scattering and guides the two-dimensional fluorescence signals along the vertical direction of its fibers. In one embodiment, the thickness of fiber-optical faceplate 308 may be between 0.5 millimeters and 3 millimeters which thermally isolates the 40-60° C. microarray assay from CMOS chip 101 and also creates adequate distance between the solution and chip 101 without any significant signal loss. The exposed surface of fiber-optical faceplate 308 may be polished glass ($SiO_2$) 309 which is ideal for DNA capturing probe attachments using standard aldehyde-modified surfaces.

As stated above, on top of chip 101 resides a thin film dielectric optical filter 307 which blocks the excitation light, while only taking emission light from fluorophores 107 (e.g., Cy3 in this case) (indicated by arrows in silicon dioxide region 305). As also stated above, on top of filter 307 resides fiber-optic faceplate 308, which brings the bottom surface image (in this biosensor case, transducers integrated within CMOS chip 101) to the top surface where biological analytes will be spotted in this case. Fiber-optic faceplate 308 may provide a good surface platform for DNA capturing probe attachments 106 while minimizing loss of signal due to the distance between the detectors (e.g., chip 101 on the very bottom) and the light generated by fluorophores 107 in the biological analytes. The biological analytes can be spotted on the top surface of fiber-optic faceplate 308 for the detection. As illustrated in FIG. 3, bio detection can be readily done on the single platform and the results are in digital numbers for further signal processing.

FIG. 3 further illustrates capturing layer 106 used for capturing fluorescent labels that were excited by a fluorescent excitation signal 310 with a wavelength of approximately 532 nanometers.

CMOS image sensors may use a process referred to as "direct integration" to measure the emitted light from fluorophores 107. In direct integration, the photocurrent generated in photodiode 302 is directly integrated (accumulated) on the photodiode capacitor. It is widely known in the art that direct integration can be carried out in an array format, where individual array components (i.e., pixels) measure light independently.

Figure 4:
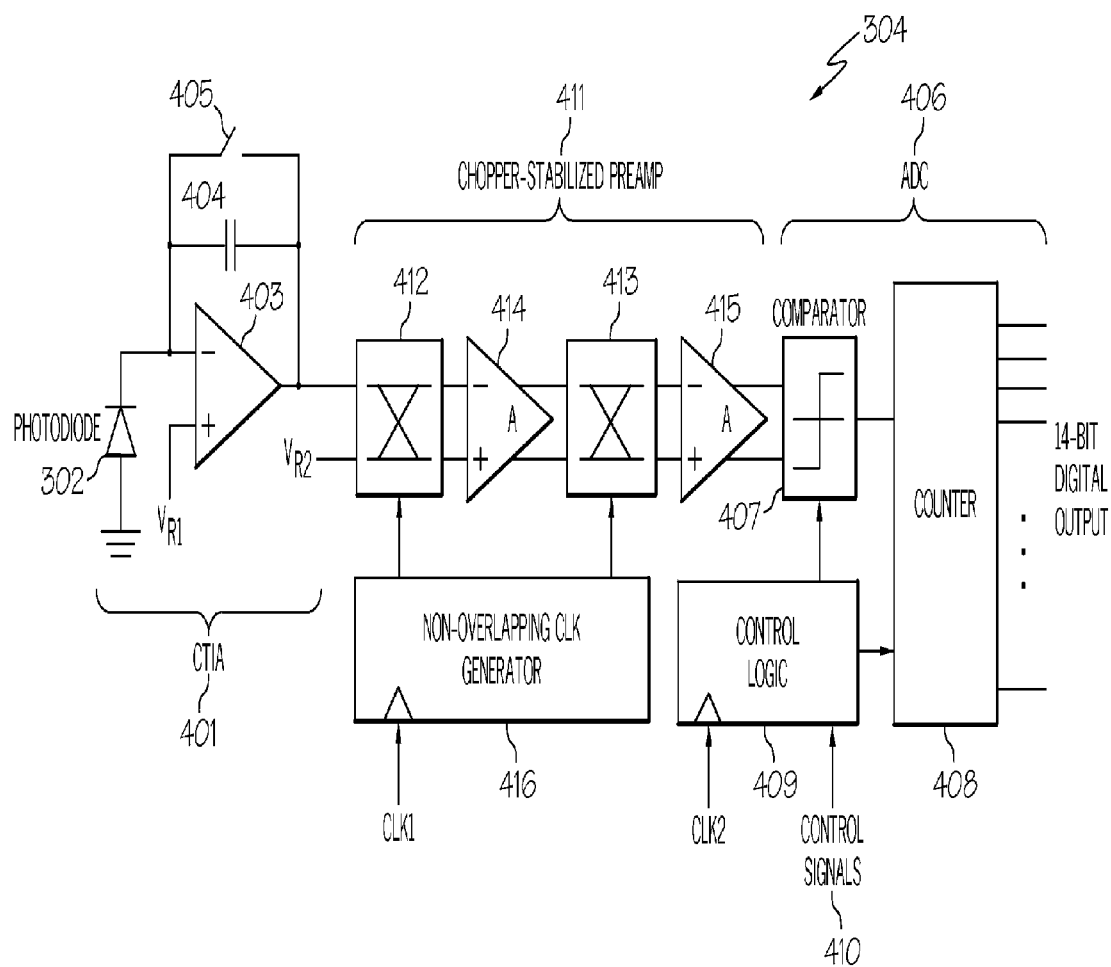
FIG. 4 illustrates an embodiment of the present invention of a pixel.

In an alternative embodiment, a capacitive transimpedance amplifier (CTIA) is used to create the photocurrent integrator as illustrated in FIG. 4. FIG. 4 illustrates an embodiment of the present invention of pixel 304. Some of the components of pixel 304 are shown in block diagram form in order not to obscure the present invention in unnecessary detail. A person of ordinary skill in the art would understand the workings of these components.

Referring to FIG. 4, in conjunction with FIG. 3, pixel 304 includes a capacitive transimpedance amplifier (CTIA) 401. CTIA 401 includes a photodiode 302, an amplifier 403 receiving an input voltage $V_{R1}$ and a capacitor 404 in the feedback mechanism of amplifier 403. Further, CTIA 401 includes a switch 405.

Unlike a direct integrator, the linearity of CTIA 401 is not limited by the photodiode junction capacitance voltage-dependency, and in addition, has a diode-independent well capacity set by feedback capacitor 404. In one embodiment, feedback capacitor 404 is a 780 femtofarad poly-to-poly capacitor. Motivated by the advantages of CMOS digital-pixel-sensor (DPS) image sensors, an analog-to-digital converter 406 (ADC) (e.g., 14 bit analog-to-digital converter) has been integrated within the pixels. ADC 406 includes a comparator 407 coupled to a counter 408 where the output of counter 408 is a 14-bit digital output. Comparator 407 and counter 408 are controlled by a control logic 409 whose actions are coordinated by clock CLK2. Control logic 409 may receive control signals 410 used to program the actions of control logic 409.

ADC 406 compares the output of CTIA 401 with the external reference voltage, $V_{R2}$, to measure the time that the ramp reaches $V_{R2}$ using comparator 407. To suppress the offset of comparator 407, a chopper stabilized preamplifier 411 may be implemented with an overall voltage gain of 60 dB gain. Chopper stabilized preamplifier 411 includes mixers 412, 413 as well as amplifiers 414, 415. Mixers 412, 413 may also be referred to as "choppers" or "modulators." Mixer 412 is the first chopper which modulates a signal to a higher frequency; whereas, mixer 413 is the second chopper which demodulates the signal back to baseband with an offset to cancel the low noise.

FIG. 4 illustrates photodiode 302 converting emitted light into electrical signal (e.g., current). Then, CTIA 401 converts this current into voltage. The feedback switch 405 in CTIA 401 shown in FIG. 4 provides extra large resistance. In a very low current input case, there will be limited finite CMOS switch resistance that prohibits the output of CTIA 401 going from the desired voltage. Switch 405 provides effectively much greater resistance than a single switch can provide while reducing the charge injections from switch 405.

Chopper stabilized pre-amplifier 411 is used to amplify the output of CTIA 401 while reducing 1/f noise of the 1$^{st}$ stage of the amplifier used in pre-amplifier 403 of CTIA 401. A non-overlapping CLK generator 416 is used to generate a clock signal to coordinate the multiplication of signal voltages by mixers 412, 413. The actions of CLK generator 416 are coordinated by clock CLK1.

The time that it takes for the voltage output of CTIA 401 to reach a certain voltage provides information about the amount of light detected by photodiode 302. In turn, the amount of light detected by photodiode 302 is proportional to the abundance of the target analytes on the surface of fiber-optical faceplate 308 (FIG. 3). In one embodiment, all entire systems aforementioned are integrated in a single pixel.

Figure 5:
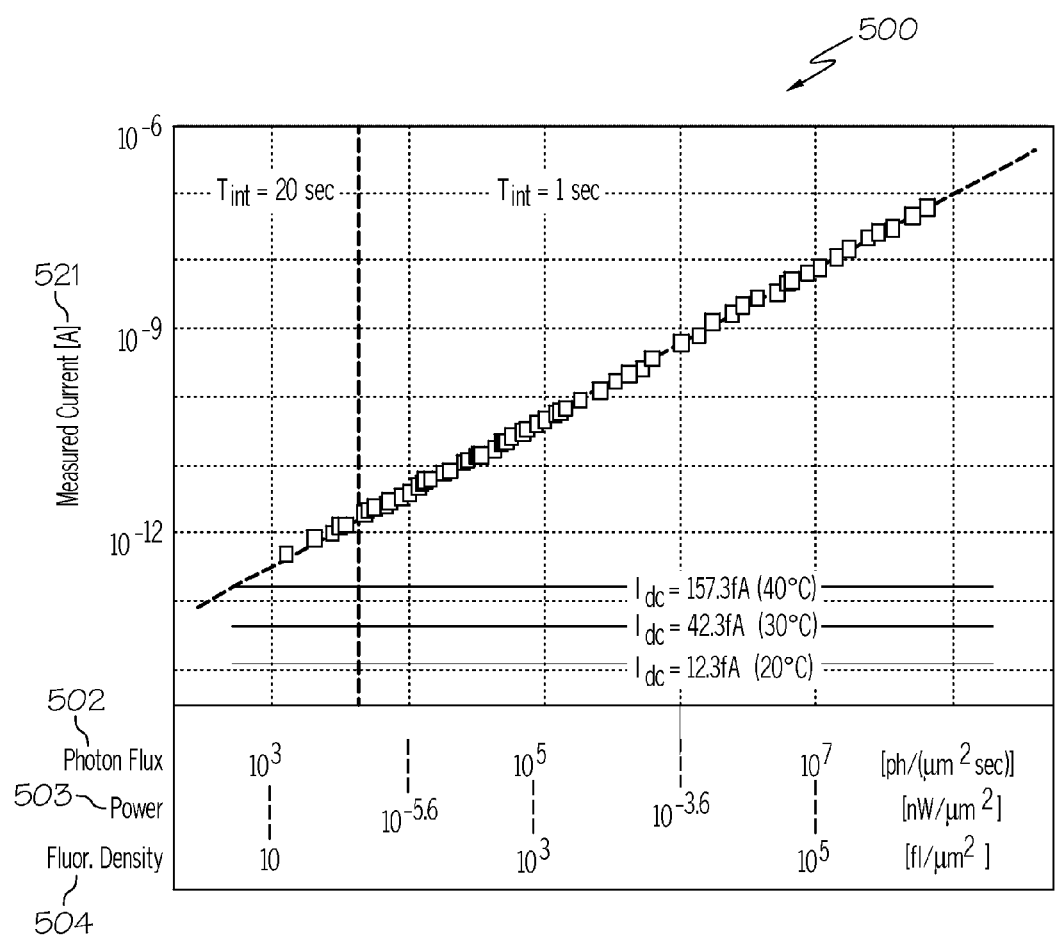
FIG. 5 is a graph illustrating the measured sensitivity of the integrated microarray and the background current present in the system as a function of temperature in accordance with an embodiment of the present invention.

FIG. 5 is a graph 500 illustrating the measured sensitivity of the integrated microarray and the background current ($I_{dc}$) present in the system as a function of temperature in accordance with an embodiment of the present invention. Referring to FIG. 5, graph 500 illustrates the measured sensitivity of the integrated microarray (as current in Amps) 501 as a function of the incident photon flux 502 (λ=532 nm), incident signal power 503 (λ=532 nm), and the estimated surface density of the fluorescent labels 504 (Cy3 label with a 3 mW excitation source). The measured dark current of each pixel 304 (FIG. 3) is approximately 12 fA at room temperature, which is much lower than the measured signals and therefore sufficiently low for typical fluorescence spectroscopy applications. FIG. 5 illustrates the sensitivity of a transducer (e.g., photodiode 302 of FIGS. 3 and 4) with CTIA 401 (FIG. 4). FIG. 5 further illustrates the "dark current" (indicated as "$I_{dc}$" in FIG. 5) that was measured at different temperatures (e.g., 20° C., 30° C., 40° C.). The dark current is the unwanted current that is typically generated by thermal agitation and leakage in photosensitive devices, such as photodiodes and charge-coupled devices. The integration time (indicated as "$T_{int}$") indicates the time that was set in pixel 304 of FIG. 4 to measure the currents of FIG. 5.

Figure 6:
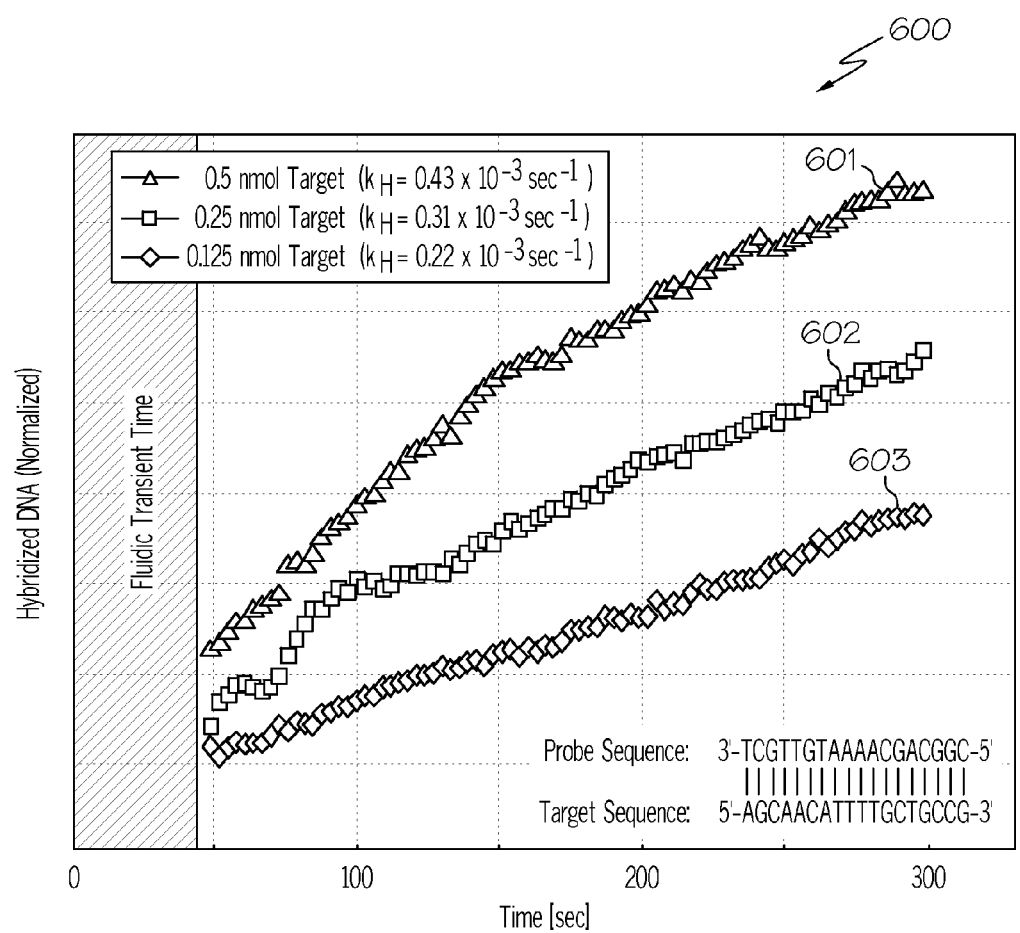
FIG. 6 is a graph illustrating the measured real-time DNA hybridization kinetics for three exemplary DNA target concentrations in solution in accordance with an embodiment of the present invention.

In addition to conventional microarray applications, system 100 (FIGS. 1A-D) is capable of real-time detection of fluorescent signals emitted from biological samples in solution. FIG. 6 is a graph 600 illustrating the measured real-time DNA hybridization kinetics for three exemplary DNA target concentrations 601, 602, 603 in solution in accordance with an embodiment of the present invention.

Referring to FIG. 6, the target strand 5'-AGCAA-CATTTTGCTGCCG-3' is labeled with Cy3 and the probe strand 3'-TCGTTGTAAAACGACGGC-5' is labeled with a black-hole quencher. The sequences are complementary so that binding occurs.

DNA target concentration 601 corresponds to a 0.5 nmol target with a $k_H$ (normalized inverse of time constant) equal to $0.43 \times 10^{-3}$ sec$^{-1}$. $k_H$ refers to the normalized inverse of time constant which shows how much bindings occur in a given time. For example, the 0.5 nmol target case has more bindings in comparison to the 0.125 nmol target case in a given time. DNA target concentration 602 corresponds to a 0.25 nmol target with a $k_H$ equal to $0.31 \times 10^{-3}$ sec$^{-1}$. DNA target concentration 603 corresponds to a 0.125 nmol target with a $k_H$ equal to $0.22 \times 10^{-3}$ sec$^{-1}$.

The results shown in FIG. 6 confirm that the measured rate of capturing is directly proportional to the analyte concentration. In one embodiment, the biosensor can detect hybridization kinetics in real-time. In a conventional microarray, washed and dried analytes labeled with fluorophores are typically used. Therefore, the researcher should wait until hybridization of DNA is done. Thus, only a steady-state response can be detected. However, in system 100 (FIGS. 1A-D), the solution can be spotted on the top of the sensor so that the detection can be performed during hybridization. Therefore, this integrated biosensor is able to detect real-time hybridization kinetic behavior. It is noted that this real-time detection does not require biosensors to be washed and waited until biological analytes get saturated. Detecting hybridization kinetic also provides information about the abundance of target analytes. In the illustrative case, all the capturing probes are labeled by fluorophores (e.g., Cy3) and the targets are labeled by quenchers, which extinct the light generated by fluorophores. The normalized results are shown in FIG. 6. The largest amount of target analytes is 0.5 nmol with the smallest time constant. FIG. 6 illustrates that larger target analytes in the solution represent the faster rising response. In summary, this type of integrated biosensor can be used for not only conventional detection (steady-state), but also real-time hybridization kinetics (transient).

The integrated biosensor of system 100 (FIGS. 1A-D) includes a fully integrated fluorescent-based microarray system. The achieved performances of this system in terms of sensitivity, compactness, versatility, and cost, satisfy the requirements of many biotechnology applications beyond DNA microarrays.

Though fluorescent based detection methods have been popularly used with microarrays, label-free detection of analytes using their intrinsic properties (e.g., charge, mass, absorption spectra) has generated a lot of interest in the research community. Label-free detection offers several advantages such as reduction in cost, omission of the molecular labeling process, feasibility of real time detection and ease of integration with standard CMOS processes.

Figure 7:
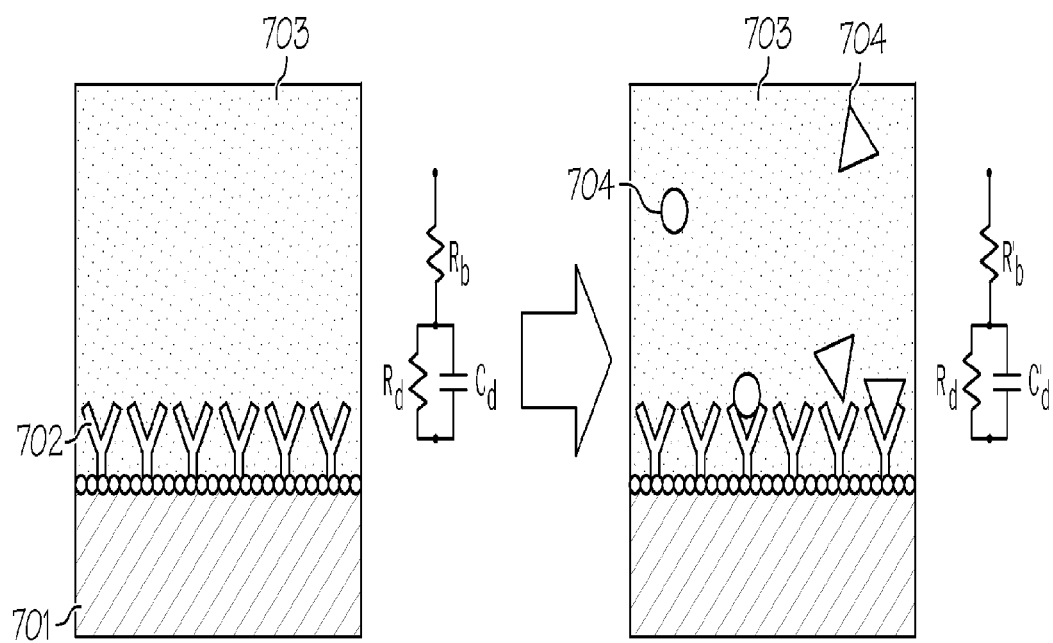
FIG. 7 illustrates impedance spectroscopy-based detection in accordance with an embodiment of the present invention.

Among the various techniques for label-free detection, impedance spectroscopy-based detection is the most compatible with current silicon-based very-large-scale integrated (VLSI) systems and integrated electronics. The concept behind this method is illustrated in FIG. 7 in accordance with an embodiment of the present invention. In this method, an electrode surface 701 is first functionalized by immobilizing probes 702 (indicated as Y's attached to top of electrode surface 701) on the electrode surface 701. Electrodes 701 are placed in an aqueous solution 703 containing analytes 704 (analytes 704 are depicted in FIG. 7 as various symbols, such as circles and triangles). Any number of analytes 704 may be present in aqueous solution 703. When analytes 704 bind to probes 702, the physiochemical characteristics of the electrode-electrolyte interface changes which subsequently results in changes in the impedance of the interface. It is known in the art that such changes in the impedance of the interface can be measured using an electronic sensor and the results can be related to the binding events, their frequency, and their abundance. As illustrated in FIG. 7, there are three important terms contributing to the impedance: $R_b$, the resistance of the solution and the impedance of the double layer represented by $R_d$ and $C_d$. On the right of FIG. 7, the $R_b'$, $R_d'$ and $C_d'$ indicate the modified values due to analyte binding. The spectroscopy-based detection is known as "impedance" spectroscopy-based detection to signify the interest in the changes in both the resistance and the capacitance of the interface as a function of excitation frequency. As impedance is a purely electrical quantity, one of the key advantages of this method is that all the signals are completely in the electronic domain. This attractive feature enables straightforward integration with standard CMOS processes.

In an illustrative design using the principles of the present invention, a 10×10 array of impedance sensors is integrated with the detection circuitry (shown in FIG. 10) for sensing the impedance of the interface between electrode 701 and electrolyte. Some innovative aspects of the design include the use of on-chip sensing electrodes and simple detection circuitry which is present underneath each of electrodes 701, permitting large-scale integration and high packing density. Another innovative aspect is that the whole chip, including the sensors, may be fabricated using 0.35 µm standard CMOS process. Since CMOS process is widely used in digital integrated circuits, large scale production of "integrated impedance sensors" could lead to significant lowering of costs.

Figures 8A, 8B:
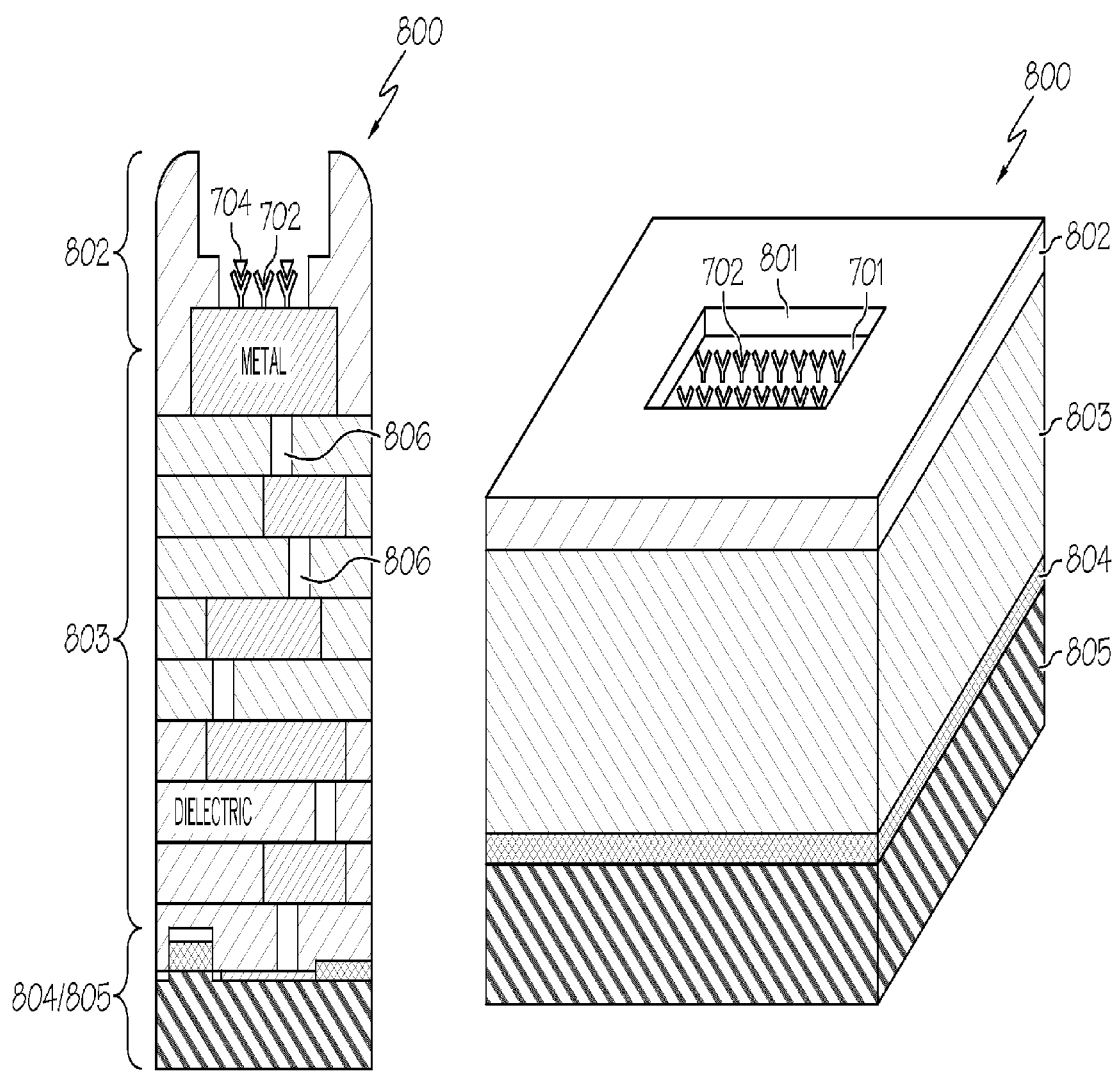
FIGS. 8A-B illustrate a pixel with an on-chip electrode that is formed by creating an opening in a passivation layer covering the metal layers in accordance with an embodiment of the present invention.

FIGS. 8A-B illustrate a pixel 800 with on-chip electrode 701 (FIG. 7) that is formed by creating an opening 801 in a passivation layer 802 covering the metal layers plus dielectric layer 803 in accordance with an embodiment of the present invention. Referring to FIGS. 8A-B, in conjunction with FIG. 7, in a CMOS process, active devices 804 are fabricated on a silicon substrate 805, and 3-4 metal layers, which are used to route various signals, are stacked on top of these active devices 804. FIG. 8A further illustrates vias 806 used to interconnect various layers. Passivation layer 802 covers the top layer of metal layers 803 in order to protect metal layers 803 and devices 804 underneath from the outside environment. An opening 801 in passivation layer 802 exposes the top layer of metal layers 803 to an aqueous solution of affinity-based biosensors, which is used as the sensing electrode 701. Capturing probes 702 are attached to sensing electrode 701. In one embodiment, passivation layer 802 has a thickness of approximately 2 micrometers.

Figure 9:
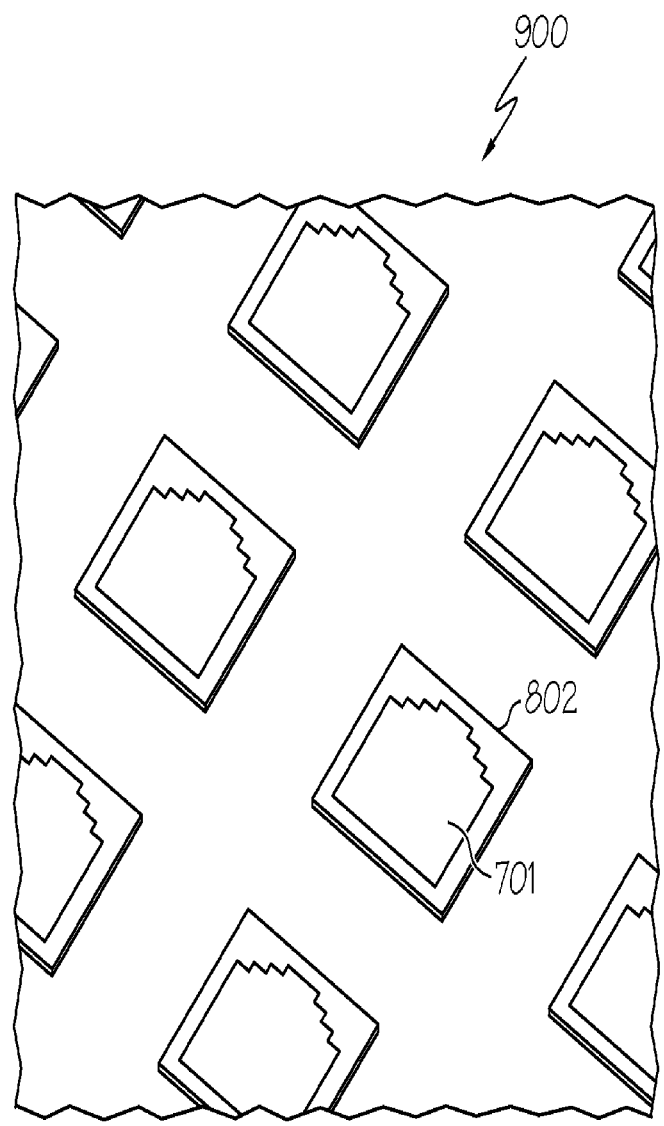
FIG. 9 illustrates a scanning electron microscope (SEM) photograph of a surface of the fabricated pixel of FIGS. 8A-B in accordance with an embodiment of the present invention.

FIG. 9 illustrates a scanning electron microscope (SEM) photograph 900 of a surface of the fabricated pixel 800 (FIGS. 8A-B) in accordance with an embodiment of the present invention. Referring to FIG. 9, in conjunction with FIGS. 7-8, in one embodiment, electrode 701 is roughly of the size 40 µm×40 µm. In one embodiment, the edges of electrode 701 are rounded off in order to approximate a circle since a drop placed on top of electrode 701 tends to take a circular shape. In one embodiment, electrodes 701 are spaced approximately 50 µm apart. In one embodiment, the die area is approximately 2 mm×2 mm.

Figure 10:
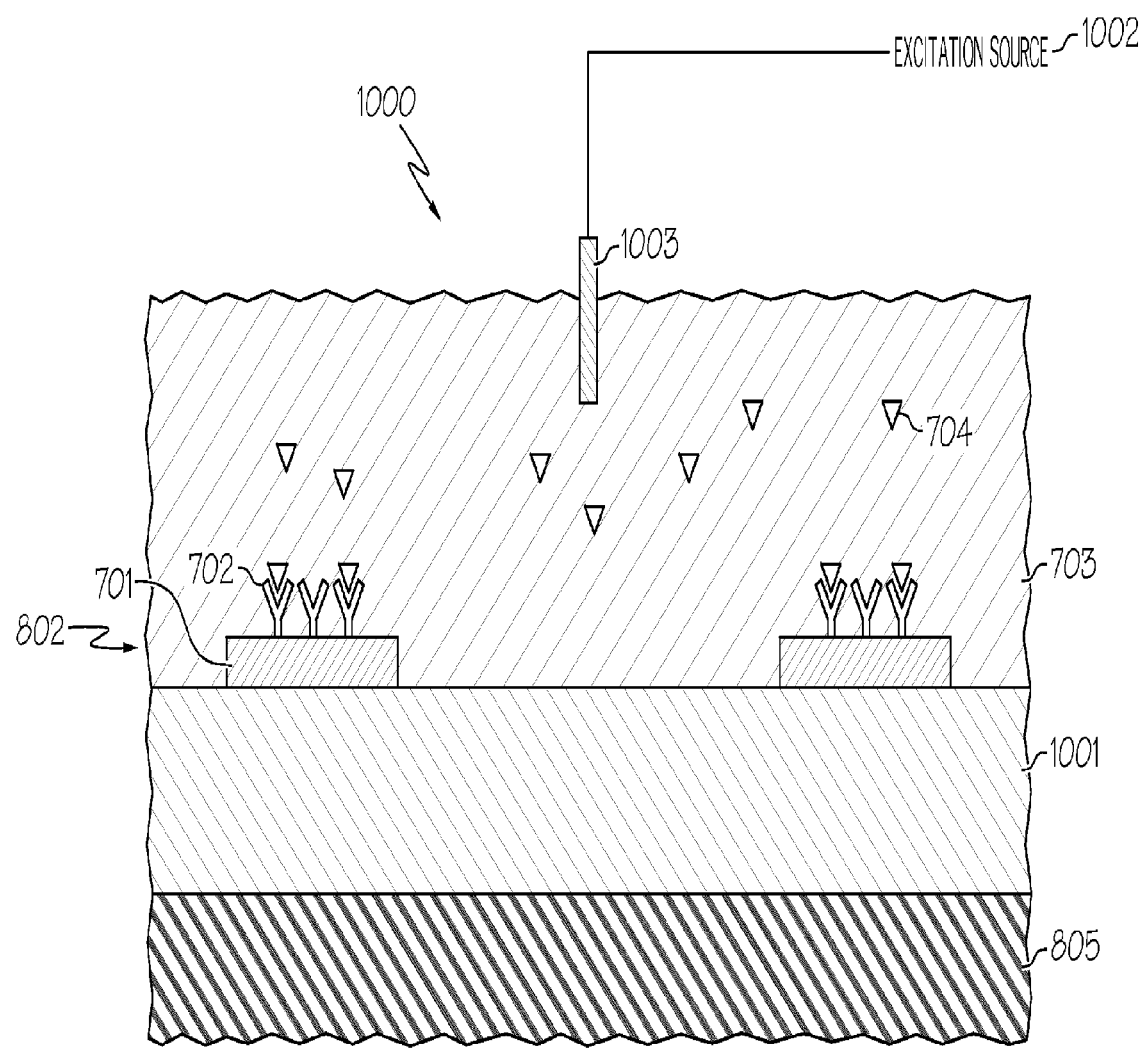
FIG. 10 illustrates the excitation scheme of a chip in accordance with an embodiment of the present invention.

FIG. 10 illustrates the excitation scheme of a chip 1000 in accordance with an embodiment of the present invention. Referring to FIG. 10, in conjunction with FIGS. 7 and 8, the surface of electrodes 701 is functionalized with capture probes 702. Solution 703 containing analytes 704 is dropped on top of a detection circuitry 1001 residing on silicon substrate 805 of chip 1000. In measuring the impedance of the system, an excitation source 1002, which is a sinusoidal function generator, is used to generate sine waves in the frequency range from a 0.01 Hz to 500 MHz. In one embodiment, excitation source 1002 typically generates sine waves in the frequency range between 10 Hz to 10 MHz. The excitation signal may be applied to an Ag/AgCl electrode 1003 which is dipped in solution 703. The impedance of the interface may be measured by detection circuitry 1001.

Figure 11:
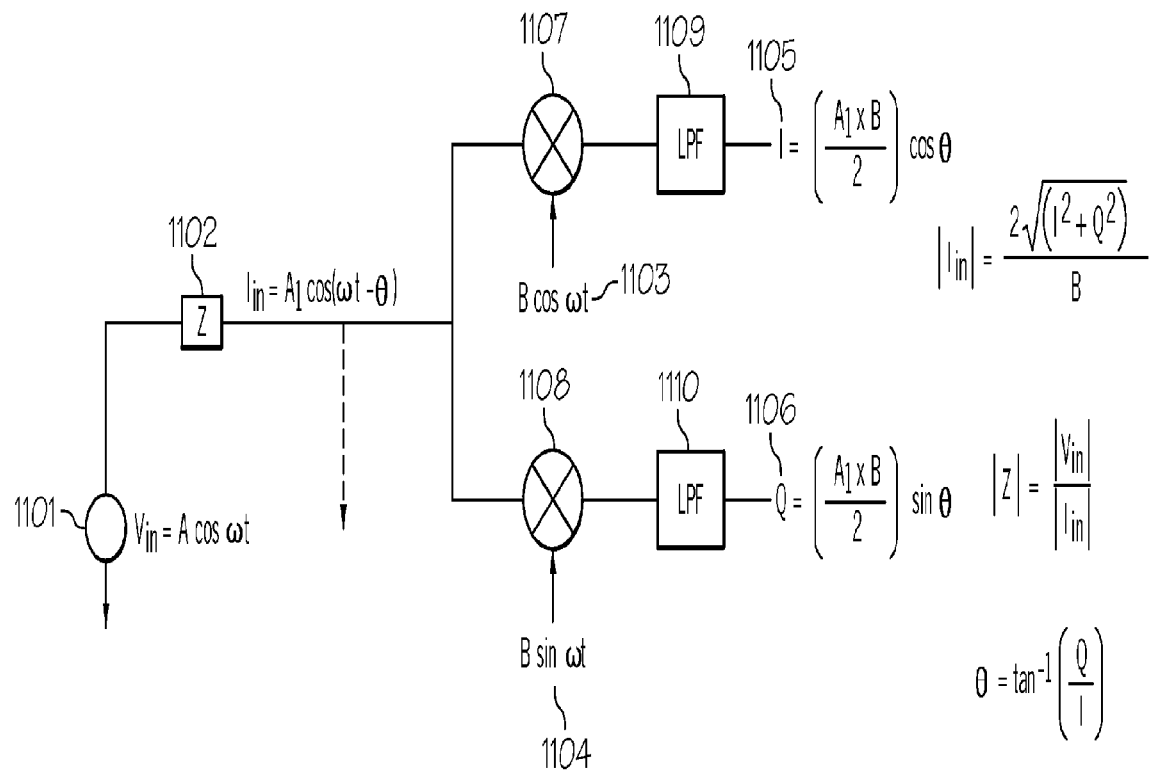
FIG. 11 illustrates the basic concept used in measuring impedance by the detection circuitry in accordance with an embodiment of the present invention.

FIG. 11 illustrates the basic concept used in measuring impedance by detection circuitry 1001 (FIG. 10) in accordance with an embodiment of the present invention. Referring to FIG. 11, the input sinusoid Vin=A cos ωt 1101 is applied as the excitation source. The impedance Z 1102 represents the sum of the solution resistance and the interface impedance. The current flowing through Z is given by $$I = \frac{V}{Z} = A1\cos(\omega t - \theta) \tag{3}$$

This current is multiplied by two sinusoidal signals B cos ωt 1103 and B sin ωt 1104, which have the same frequency of the excitation source. The path in which the multiplication with B cos ωt is called I path 1105. The other path is generally referred to as the Q path 1106. After multiplication by multipliers 1107, 1108 and subsequent low pass filtering by low pass filters 1109, 1110, a signal proportional to cos θ is generated in I path 1105, while the signal proportional to sin θ is generated in Q path 1106. Using these two signals, it is possible to calculate both the magnitude and phase of the complex impedance denoted by Z in FIG. 11.

Figure 12:
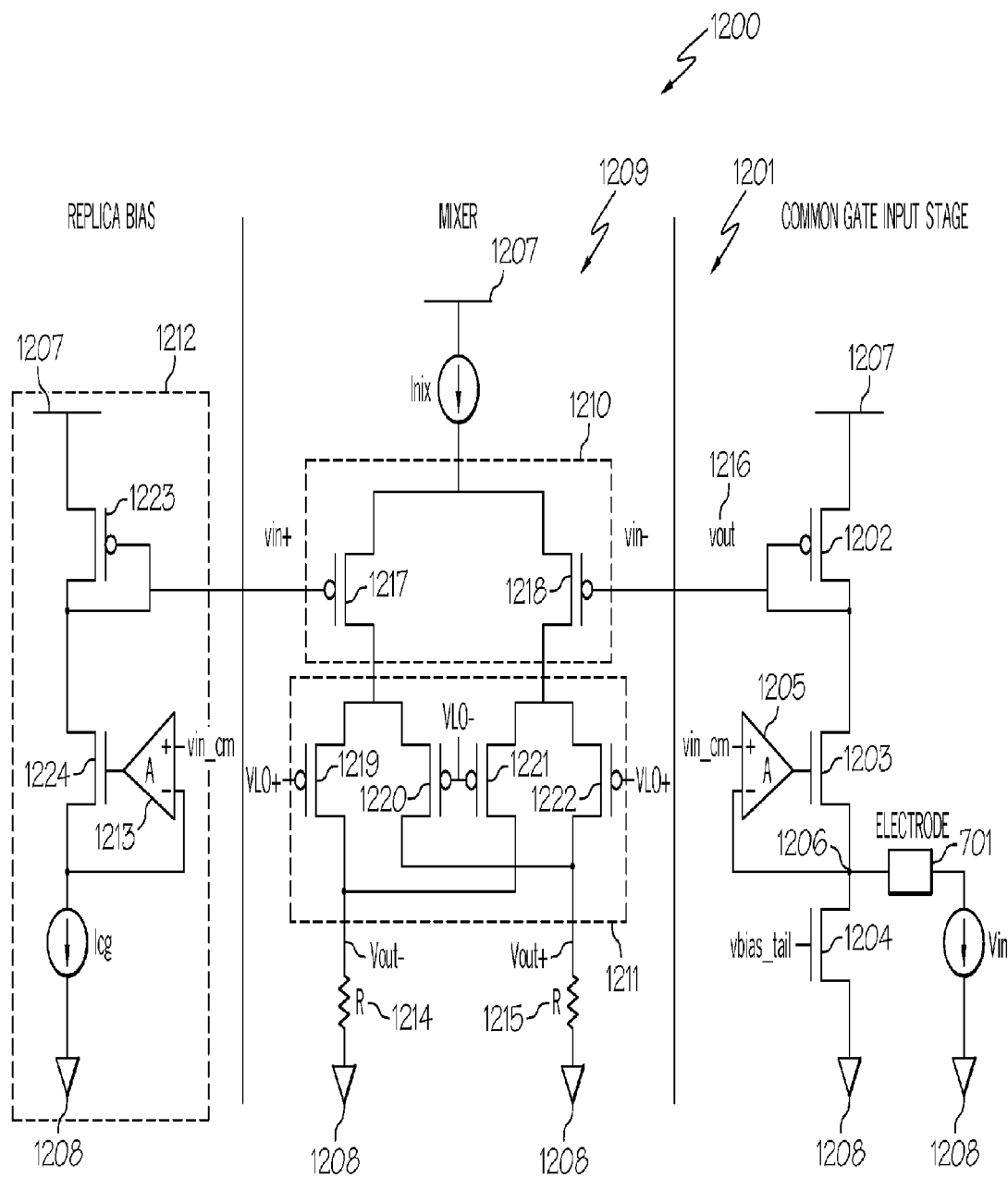
FIG. 12 illustrates a circuit for the each individual pixel in accordance with an embodiment of the present invention.

FIG. 12 illustrates a circuit 1200 for the each individual pixel 800 (FIGS. 8A-B) in accordance with an embodiment of the present invention. Referring to FIG. 12, in conjunction with FIGS. 7, 8 and 11, circuit 1200 includes a common gate input stage 1201 which includes a p-type transistor 1202 coupled to n-type transistors 1203, 1204. The gate of n-type transistor 1203 is coupled to a differential amplifier 1205.

Electrode 701 is connected to input node 1206 of common gate amplifier 1205. Electrode 701 is coupled to the input voltage ($V_{in}$). The gate of n-type transistor 1204 is biased with a signal labeled "vbias_tail." The negative input of common gate amplifier 1205 is coupled to node 1206; whereas, the positive input of common gate amplifier 1205 receives an input voltage labeled "vin_cm." The source of p-type transistor 1202 is coupled to power supply 1207; whereas, the source of n-type transistor 1204 and $V_{in}$ are coupled to ground 1208.

Circuit 1200 additionally includes a mixer 1209. Front-end amplifier 1201 and mixer 1209 may be implemented on-chip while other components (e.g., low pass filter and signal processing blocks) may be implemented off-chip in order to reduce the area of pixel 800.

In one embodiment, common gate input stage 1201 presents a low input impedance below 100 ohms for the entire frequency range from DC to 50 MHz. This is achieved by further reducing the transconductance of input transistor 1202 using a simple differential amplifier 1205 as the gain-boosting circuitry. Another important function of differential amplifier 1205 is that it helps to set the DC potential at electrodes 701. This helps in maintaining zero DC potential between the working electrode common to all the electrodes and the on-chip electrode. The current flowing through input stage 1201 is transferred using current mirrors 1210 to a set of double-balanced Gilbert-cell mixers 1211. Double-balanced Gilbert cell mixers 1211 are adopted to suppress the component at the signal frequency caused by I and Q square waves 1105, 1106 applied to mixer 1209. To minimize mismatch, an exact replica of input circuit 1201 (circuit 1212) is used carrying the same amount of current but with no input being applied. The only exception is that differential amplifier 1213 used in replica bias circuit 1212 has lesser current. Furthermore, resistors 1214, 1215 are used in the load of mixer 1209 in order to minimize the flicker noise (1/f noise) at output 1216.

Mixer 1209 additionally includes a current source identified by "Inix" that is inputted to current mirrors 1210. The gate of the transistors 1217, 1218 of current mirrors 1210 receives an opposite input voltage, vin+ and vin−, respectively. The drains of transistors 1217, 1218 are coupled to the sources of transistors 1219, 1220, 1221, 1222 of mixers 1211. The gates of transistors 1219, 1222 receive a positive oscillator voltage (identified as "VLO+"); whereas, the gates of transistors 1220, 1221 receive a negative oscillator voltage (identified as "VLO−"). The negative and positive output voltage of mixers, identified as "Vout−" and "Vout+," respectively, are coupled to resistors 1214, 1215, respectively. Resistors 1214, 1215 are coupled to ground 1208.

As discussed above, circuit 1212 is a replica of input circuit 1201. Circuit 1212 includes a p-type transistor 1223 coupled to power supply 1207. The gate of transistor 1223 is coupled to the gate of transistor 1217. The drain of transistor 1223 is coupled to the source of n-type transistor 1224. The gate of transistor 1224 is coupled to differential amplifier 1213 with its negative input coupled to the source of transistor 1224. The positive input of differential amplifier 1213 receives the input voltage labeled "vin_cm." The source of transistor 1224 is coupled to a current source labeled "Icg" which is coupled to ground 1208.

The pixel level performance metrics using the components of circuit 1200 are shown in Table I.

TABLE I

| Performance metrics of pixel 304 | |
|---|---|
| Gain of the cell | 90 dB |
| Bandwidth | 10 Hz-50 MHz |
| Noise at the output referred to the input current | <0.4 nA rms over 100 Hz bandwidth |
| Input impedance | <100 ohm from dc to 50 MHz at all corners |
| Max input current | 20 µA |
| Current consumption | 210 µA at 3.3 V supply |

In one embodiment, circuit 1200 has a current to voltage gain of 90 dB and the input referred noise current is less than 0.2 nA rms for 100 Hz bandwidth. In one embodiment, each pixel 800 consumes 210 µA of current with a 3.3V power supply. In one embodiment, the maximum input current for the circuit remains linear at 20 µA.

Although the systems are described in connection with several embodiments, it is not intended to be limited to the specific forms set forth herein, but on the contrary, it is intended to cover such alternatives, modifications and equivalents, as can be reasonably included within the spirit and scope of the invention as defined by the appended claims.

The invention claimed is:

1. A biosensor system, comprising:
a silicon substrate;
active devices fabricated on said silicon substrate;
a plurality of metal layers integrated on top and adjacent to said active devices;
a passivation layer covering a top metal layer of said plurality of metal layers in order to protect said plurality of metal layers, wherein said passivation layer comprises an opening configured to expose said top metal layer to an environment, wherein said opening is used as a sensing electrode, wherein said sensing electrode is located in an electrolyte containing analytes, wherein said sensing electrode is configured to detect a change in an impedance at an interface between said sensing electrode and said electrolyte in response to an analyte of interest binding to one of said plurality of probes; and
a plurality of probes attached to said sensing electrode, wherein said plurality of probes are impedance sensors;
a detection circuitry residing on said silicon substrate, wherein said electrolyte containing analytes resides on top of said detection circuitry, wherein said detection circuitry is configured to measure said impedance at said interface between said sensing electrode and said electrolyte;
an excitation source configured to generate sine waves; and
an excitation electrode connected to said excitation source, wherein said excitation electrode resides in said electrolyte.

2. The biosensor system as recited in claim 1, wherein a sinusoidal signal is applied as said excitation source, wherein current traveling through said interface is multiplied by a first and a second periodic signal having a same frequency as said excitation source but with a pre-defined phase difference, wherein a first output signal is generated by multiplying said current with said first periodic signal, wherein a second output signal is generated by multiplying said current with said second periodic signal, wherein a magnitude and a phase of a complex impedance at said interface is measured using a low frequency part of said first and second output signals.

3. The biosensor system as recited in claim 1 further comprising: impedance sensors for sensing said impedance of said interface, wherein said impedance sensors are integrated in an array format.

4. The biosensor system as recited in claim 1, wherein said excitation electrode is an Ag/AgCL electrode.

5. The biosensor system as recited in claim 4, wherein said excitation source generates sine waves in a frequency range from 0.01 Hertz to 500 Megahertz.

* * * * *